(12) United States Patent
Tippett

(10) Patent No.: US 7,728,188 B2
(45) Date of Patent: Jun. 1, 2010

(54) METHODS AND COMPOSITIONS FOR TOPICAL WOUND TREATMENT

(76) Inventor: Aletha Tippett, 10304 Peachtree La., Cincinnati, OH (US) 45242

( * ) Notice: Subject to any disclaimer, the term of this patent is extended or adjusted under 35 U.S.C. 154(b) by 371 days.

(21) Appl. No.: 11/619,903

(22) Filed: Jan. 4, 2007

(65) Prior Publication Data

US 2007/0104770 A1    May 10, 2007

Related U.S. Application Data

(62) Division of application No. 10/367,393, filed on Feb. 14, 2003, now abandoned.

(60) Provisional application No. 60/420,008, filed on Oct. 21, 2002.

(51) Int. Cl.
*A61F 13/00* (2006.01)
*A61L 15/16* (2006.01)

(52) U.S. Cl. .......................... 602/48; 602/46; 424/443; 424/444; 424/446; 424/447

(58) Field of Classification Search ............... 602/48, 602/46, 41, 42, 43, 44, 45, 47, 49, 50–59; 424/443–449, 78.06, 78.07, 78.05; 604/289, 604/304, 307
See application file for complete search history.

(56) References Cited

U.S. PATENT DOCUMENTS

| | | | | |
|---|---|---|---|---|
| 3,783,869 A | * | 1/1974 | Schnipper | 604/304 |
| 4,261,982 A | * | 4/1981 | Luedders et al. | 514/29 |
| 4,588,400 A | * | 5/1986 | Ring et al. | 604/304 |
| 5,061,689 A | * | 10/1991 | Alvarez | 514/6 |
| 5,407,670 A | * | 4/1995 | Shinault | 424/78.06 |
| 5,516,808 A | * | 5/1996 | Sawaya | 514/781 |
| 5,804,213 A | * | 9/1998 | Rolf | 424/445 |
| 6,194,455 B1 | * | 2/2001 | Wharton | 514/532 |
| 6,599,525 B2 | * | 7/2003 | Scamilla Aledo et al. | 424/445 |
| 2004/0022863 A1 | * | 2/2004 | Hamtini | 424/523 |

FOREIGN PATENT DOCUMENTS

WO    WO 0044367 A2 *   8/2000

* cited by examiner

*Primary Examiner*—Patricia M Bianco
*Assistant Examiner*—Ophelia Hawthorne
(74) *Attorney, Agent, or Firm*—Dinsmore & Shohl LLP

(57) ABSTRACT

Methods for improved treatment of wounds on a patient. Method includes locally administering a healing composition to the skin wound such that the healing of the skin wound is enhanced. The healing composition includes from about 5 mg to about 40 mg lidocaine hydrochloride per gram of the healing composition, from about 250 units to about 2000 units polymyxin B sulfate per gram of the healing composition, and from about 10 units to about 100 units bacitracin zinc per gram of the healing composition.

19 Claims, 6 Drawing Sheets

METHODS AND COMPOSITIONS FOR TOPICAL WOUND TREATMENT

RELATED APPLICATIONS

The present application is a Divisional patent application of co-pending U.S. application Ser. No. 10/367,393 filed Feb. 14, 2003 which claims priority under 35 U.S.C. §119 of U.S. Provisional Application Ser. No. 60/420,008 filed Oct. 21, 2002. The aforementioned applications are hereby incorporated herein by reference.

TECHNICAL FIELD

The present invention relates generally to methods and compositions for treating patients, and more particularly to a method and composition for topical wound treatment.

BACKGROUND OF THE INVENTION

Wounds are commonplace from childhood to old age. Wounds are a significant problem among the geriatric and nursing home population, especially at the end of life. Pressure ulcers alone exact a tremendous human and financial toll, costing on average more than $1,200 per patient per month to treat. The prevalence of pressure ulcers in 1997 was 16 of every 1,000 nursing home residents. A goal of a federal program, "Healthy People 2010" is a reduction of pressure ulcers to a prevalence of less than 8 per 1,000. Diabetic ulcers similarly result in significant morbidity and costs, with diabetics accounting for approximately 82,000 amputations annually in the U.S., averaging $30,000 per amputation. Other wounds plaguing the nursing home and end of life population are ulcers resulting from arterial and venous insufficiency, as well as traumatic wounds, and non-healing surgical wounds.

Most of the wounds treated are chronic wounds, often persisting for many months. Especially among the terminally ill, there is little expectation of healing a wound due to the population being malnourished, immobile and with many comorbidities that inhibit and delay wound healing. In addition, often the patient will not live long enough to heal a wound. In the terminally ill patient, the goal typically is palliation, including relief of pain, and prevention of infection. A chronic wound is any break, or ulceration, of the skin that is of long duration or recurs frequently and has not responded to conventional therapies.

Standard wound care involves debridement, cleansing and covering the wound with any of a variety of commercially available dressings. There are many special dressings available which are designed to keep wounds moist or absorb exudates. Some specialty dressings have silver impregnated in the dressing to prevent infection. Typically dressings are attached either with self-adhesive or tape, or in some cases are applied with a compression wrap. Recent high tech approaches are available for wound care using thermal wound treatments and vacuum pumps. While these can be effective, they are very expensive and healing times are still measured in weeks or months. As such, it is desired to have an inexpensive wound treatment method and composition which reduces the time required for wounds to heal.

SUMMARY OF THE INVENTION

Accordingly, it is an object of the present invention to provide novel methods and compositions for topical wound care which overcomes one or more disadvantages of the prior art.

It is a more specific object of the invention to provide novel methods and compositions for improved treatment of wounds on a patient utilizing lidocaine.

These additional objects and advantages are provided by the methods and compositions of improved treatment of wounds on a patient of the present invention.

More particularly, a method and composition are provided for improved treatment of wounds on a patient. The composition comprises a safe and effective amount of lidocaine in a carrier, wherein the composition is topically applied to a wound on a patient.

In another embodiment of the present invention, a composition for improved treatment of wounds on a patient is provided. The composition comprises a safe and effective amount of lidocaine in a carrier and a safe and effective amount of a topical antibiotic compound, wherein the composition is topically applied to a wound on a patient.

In another embodiment, the present invention is directed to a wound dressing comprising a bandage, a safe and effective amount of lidocaine in a carrier, wherein the wound dressing enhances healing of a wound.

Also provided is a method for treating a patient having a skin wound, including the steps of locally administering a safe and effective amount of lidocaine in a carrier to the skin wound such that the healing of the skin wound is enhanced.

Another aspect of the present invention is an article of manufacture comprising packaging material and a composition comprising a safe and effective amount of lidocaine in a carrier, wherein the packaging material comprises a label that indicates the composition is useful for treating a patient having a skin wound, and wherein local administration of the composition enhances healing of a skin wound.

Another aspect of the present invention is a method for treating a patient having a skin wound. The method includes the steps of applying a zinc oxide ointment around the external of the wound; applying lidocaine in a carrier to a dressing; applying the dressing to the wound; and securing the dressing to the patient.

Still other objects, advantages and novel features of the present invention will become apparent to those skilled in the art from the following detailed description, which is simply by way of illustration various modes contemplated for carrying out the invention. As will be realized, the invention is capable of other different obvious aspects, all without departing from the invention. Accordingly, the drawings and descriptions are illustrative in nature and not restrictive.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE PREFERRED EMBODIMENT

Figure 1:
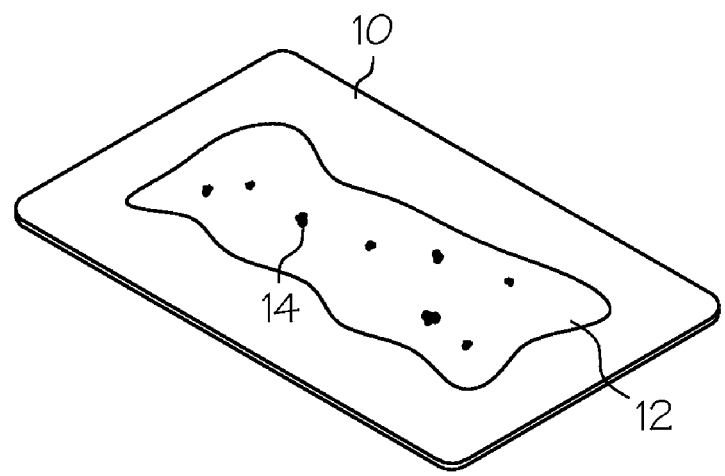
FIG. 1 is a schematic illustration of an exemplary wound care dressing according to an embodiment of the present invention.

Reference will now be made in detail to various embodiments of the invention, examples of which are illustrated in the accompanying drawings, wherein like numerals indicate similar elements throughout the views.

A novel wound care treatment has been developed which uses a composition comprising a safe and effective amount of lidocaine in a carrier, wherein the composition is topically applied to a wound on a patient. The phrase "safe and effective amount", as used herein, means the amount of that component sufficient to significantly positively modify the condition to be treated, but low enough to avoid serious side effects (at a reasonable benefit/risk rational), within the scope of sound medical judgment. A safe and effective amount of the component will vary with the specific component which is employed, the ability of the composition to penetrate the component through the skin, the amount of the composition, the particular type of wound being treated, the age and physical condition of the patient being treated, the severity of the wound, the duration of the treatment, the nature of concurrent therapy, and like factors. In one exemplary embodiment, the lidocaine is viscous lidocaine. Other forms of lidocaine, such as injectable solution of lidocaine are also considered. The carrier may be any carrier known to one skilled in the art such as aqueous-based or oil-based carriers. Exemplary carriers include water and saline solution.

In an exemplary embodiment of the present invention, the composition comprises from about 5 mg to about 40 mg lidocaine hydrochloride per gram of the composition, more preferably from about 18 mg to about 25 mg lidocaine hydrochloride per gram of the composition and most preferably from about 18 mg to about 20 mg lidocaine hydrochloride per gram of the composition.

In one embodiment of the present invention, the composition further comprises a safe and effective amount of at least one topical antibiotic compound. The antibiotic compound is believed effective in preventing infection and may help promote healing. It is believed that there may be some theoretical inhibition of healing by lidocaine with subsequent increase in an infection and the addition of the antibiotic agent will counter that effect.

Exemplary topical antibiotic classes which may be employed include aminoglycosides, antifungals, carbapenems, cephalosporins, macrolides, penicillins, quinolones, sulfonamides, tetracyclines, chloramphenicol, clindamycin, metronidazole, nitrofurantoin, and vanomycin. Other classes of compounds which may be employed include antimalarials, antimycobacterials, antiparasitics, antiviral agents (such as anti-CMV, anti-herpetic, anti-HIV and anti-influenza) and dermatologic antibacterials (such as bacitracin, polymyxin, mafenide, mupirocin and silver sulfadiazine).

Exemplary topical antibiotic compounds which may be employed include chloramphenicol, chlortetracycline, clindamycin, erythromycin, gramicidin, gentamicin, metronidazole, mupiroicin, neomycin, polymyxin B, bacitracin, silver sulfadiazine, tetracycline, or combinations thereof. In addition, metronidazole is beneficial as the topical antibiotic, especially when odor of the wound is a problem. Crushed metronidazole tablets can be applied to the composition of the present invention.

In another exemplary embodiment of the present invention, the composition comprises from about 5 mg to about 40 mg lidocaine hydrochloride, about 250 units to about 2000 units polymyxin B sulfate and about 10 units to about 100 units bacitracin zinc per gram of the composition; and more preferably from about 18 mg to about 25 mg lidocaine hydrochloride, about 500 to about 1000 units polymyxin B sulfate and about 25 to about 50 units bacitracin zinc per gram of the composition.

In one exemplary embodiment of the present invention, the treatment method for treatment of a wound comprises debriding the wound, if necessary, and cleaning the wound with a suitable cleaning solution, such as normal saline. Thereafter, a zinc oxide ointment may be applied to the skin around the wound. It is believed that the ointment protects the surrounding skin, promotes healing and helps to hold the dressing in place. The substrate for the dressing may be one of any known to one skilled in the art. For example, exemplary substrates include gauze, foam, gels, and other conventional medical substrate dressings. Moreover, if the wound bed needs to be kept moist, the substrate can be moistened with normal saline. Alternatively, particularly if the wound bed has exudates, dry gauze or other absorbents can be used. In addition, if the wound bed is necrotic, the gauze may be moistened with one-quarter strength Dakins solution (hypochlorite, i.e., bleach) or an enzymatic debriding agent such as collagenase (Santyl®) may be added. The dressing is then layered with lidocaine and the antibiotic and applied to the wound.

After the dressing which is layered with the lidocaine and the topical antibiotic is applied to the wound, a top dressing such as gauze or bandage can be then applied to the patient to cover the wound and dressing. The top dressing may be taped, or wrapped in place depending on the patient's skin conditions and location of the wound. If the patient's skin is fragile it may be damaged by an adhesive. In this case, a top dressing of polymer film is applied and held in place by the zinc oxide ointment that surrounds the wound. Typically, the dressing is changed daily and as needed if soiled or disturbed.

The size and type of dressing used depends on the wound. In one exemplary embodiment, for a deep narrow wound which requires packing, gauze strips can be used. Shallow wounds can be dressed with simple two by two inch or four by four inch gauze pads. Deep large wounds can be packed with fluffed gauze pads. In all cases, the gauze is layered with lidocaine and the antibiotic compound.

FIG. 1 illustrates an exemplary embodiment of the present invention. A rectangular gauze pad 10 sized to fit the wound, is layered with viscous lidocaine 12 and a topical antibiotic powder 14 is sprinkled over the lidocaine layer. Enough viscous lidocaine 12 should be applied in a thin layer to cover an area the size of the wound.

Normal gauze pads are suitable for shallow wet or dry wounds. The gauze can be dry or moist, depending on the requirements of the wound bed. The gauze can be moistened with normal saline if needed for a dry wound bed. The dressing is then applied with the side of the gauze pad having the viscous lidocaine and antibiotic powder next to the wound.

In one embodiment, a zinc oxide barrier ointment is applied to the skin around the wound prior to application of the dressing. The zinc oxide barrier protects the skin from moisture and is believed to enhance healing as well as hold the dressing in place for attachment.

Figure 2:
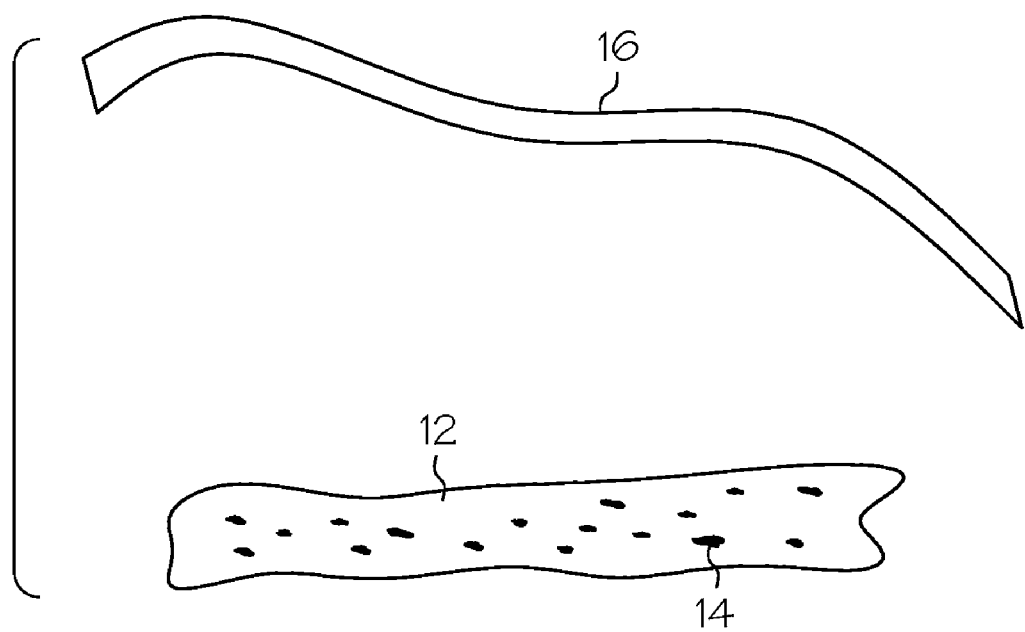
FIG. 2 is a schematic illustration of a method of preparing an exemplary wound care dressing according to an embodiment of the present invention.

Wounds vary in size and may necessitate changing the gauze substrate in order to fill dead space in the wound. FIG. 2 illustrates gauze stripping 16 that can be pulled through a pool of viscous lidocaine 12 sprinkled with a topical antibiotic powder 14. The viscous lidocaine 12 can be poured into a small pool on a non-absorbable surface and the topical antibiotic powder 14 can then be sprinkled over the lidocaine pool. The user can then pull the gauze strips through the pool using one hand to pull the strip and the other hand to push the strip into the pool of viscous lidocaine and topical antibiotic powder. The strip may then be packed into a deep narrow wound (such as those which often occur over the ischium).

Figure 3:
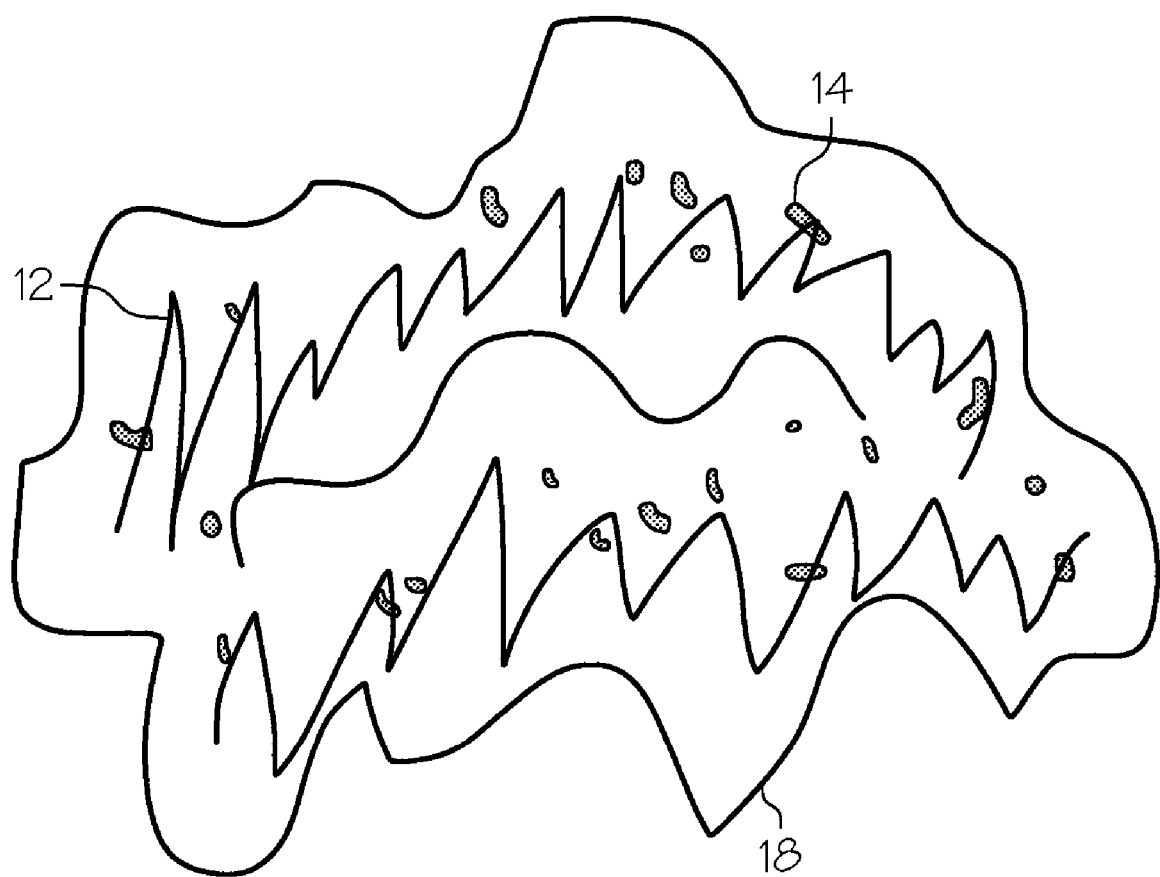
FIG. 3 is a schematic illustration of another exemplary wound care dressing according to an embodiment of the present invention.

In another embodiment, a rectangular gauze pad has the layers pulled apart to create a fluffy piece of gauze. FIG. 3 illustrates fluffed gauze 18 as the dressing. The viscous lidocaine 12 can be poured onto the fluffed gauze 18 and a topical antibiotic powder sprinkled over the viscous lidocaine on the fluffed gauze. This dressing may then be placed or packed in deep, larger wounds that require more volume to fill the wound bed than can be provided by a flat pad. Multiple fluffed pads can be used if needed to fill space in the wound. Other filling materials known to one skilled in the art may also be utilized instead of the fluffed gauze (e.g., cotton, alginates, hydrogels or cellulose).

Figure 4A:
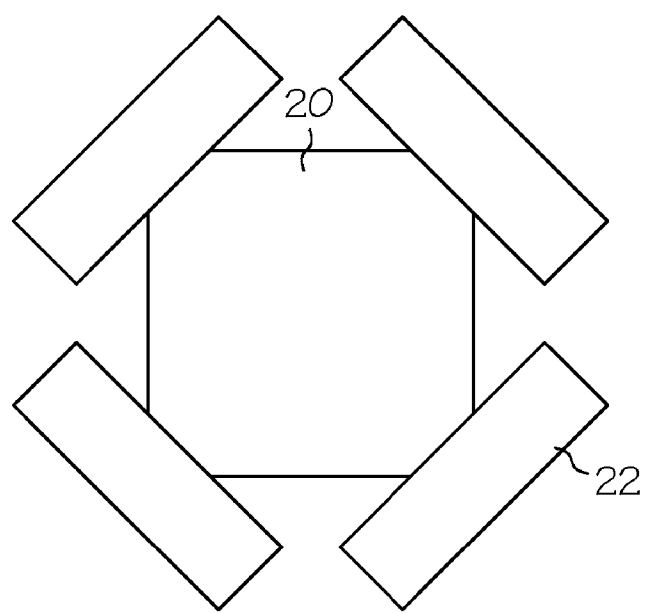
FIGS. 4A and 4B are schematic illustrations of a method of securing an exemplary would care dressing according to an embodiment of the present invention.
Figure 4B:
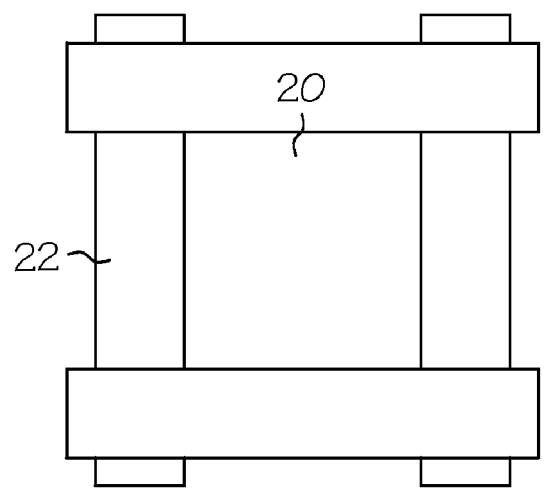
Figure 5:
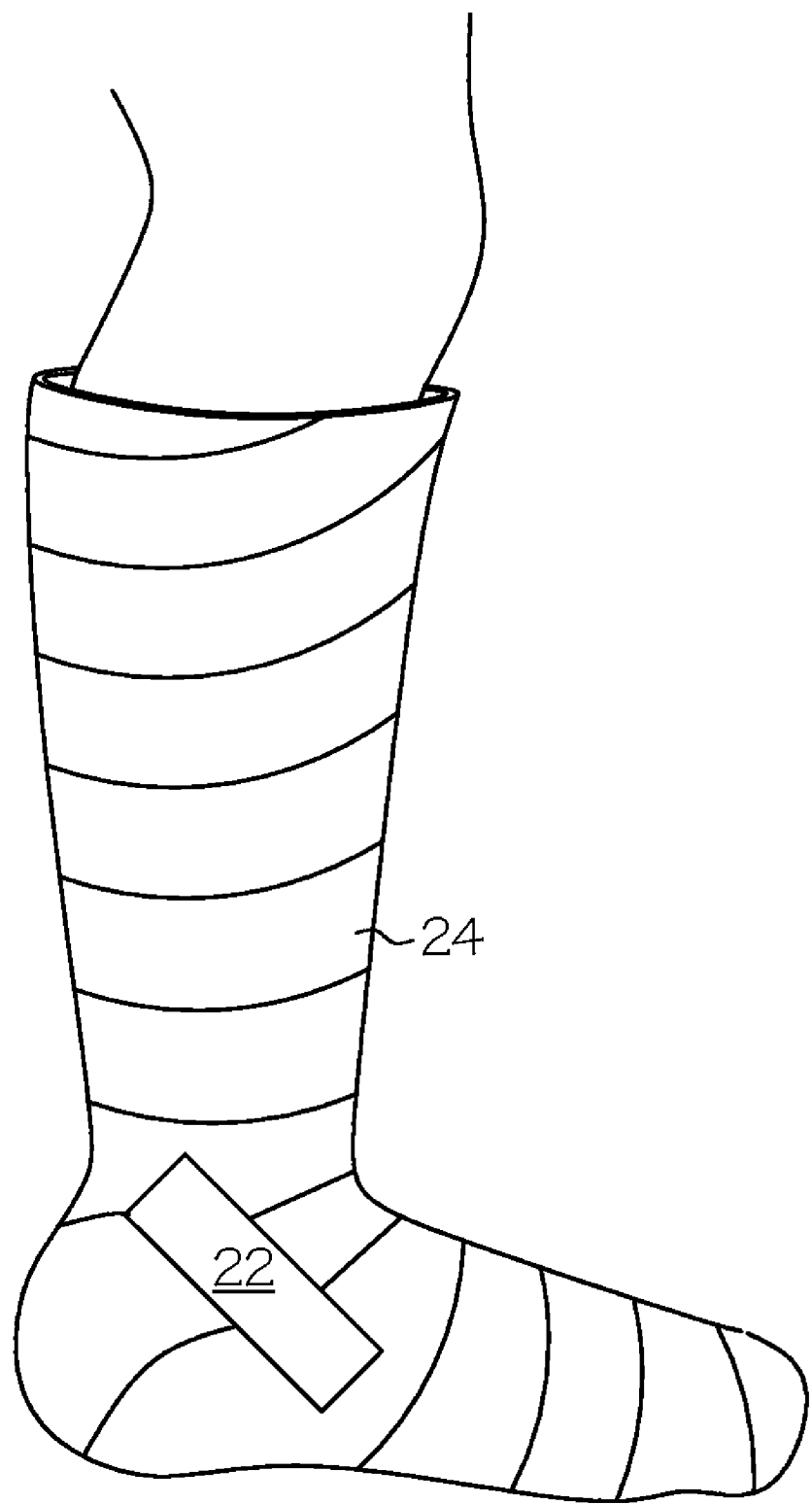
FIG. 5 is a schematic illustration of another method of securing an exemplary wound care dressing according to an embodiment of the present invention.

The dressing containing the wound care composition may be attached to the patient using various methods known to one skilled in the art. For example, as depicted in FIGS. 4A and 4B, a rectangular pad dressing may be taped in place on the patient. The tape can be placed window pane style (4B) or corner taped (4A) using medical tapes known to those skilled in the art. One disadvantage of taping is potential damage to or allergic reaction on the patient's skin by the adhesive, or the tape not sticking to the patient. An alternative method of attachment is illustrated in FIG. 5. If the wound is on an extremity, such as foot or leg, the dressing can be held in place with gauze bandage 24 circumferentially wrapped. The gauze end is then anchored with a piece of tape 22 or clipped to the under layer of gauze. The advantage of this method is that the tape adhesive does not directly touch the skin. In one exemplary embodiment of the present invention, standard covers know to one skilled in the art may be utilized (e.g., Tegaderm® available from 3M and Opsite® available from Smith & Nephew).

Figure 6:
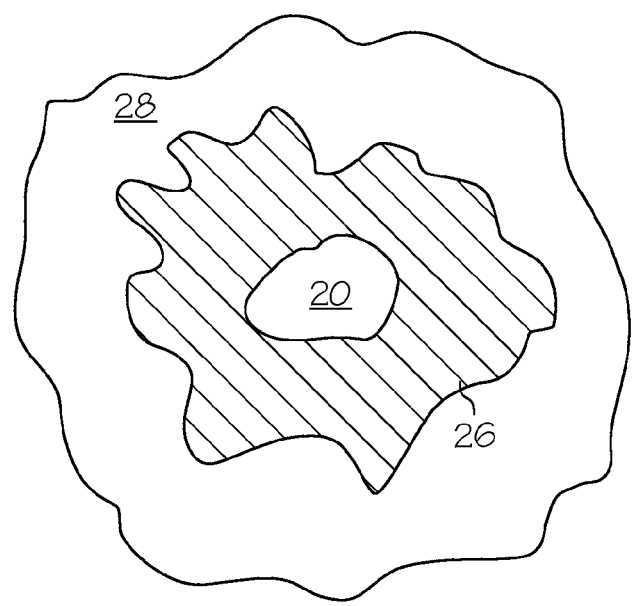
FIG. 6 is a schematic illustration of another exemplary would care dressing according to an embodiment of the present invention.

Another exemplary method of attachment of the dressing to the patient is illustrated in FIG. 6. This embodiment utilizes a polymer film 28 (e.g., Saran Wrap® available from Dow Chemical or Reynolds® Plastic Wrap available from Reynolds Metals Company) to cover the dressing 20. When the polymer film is pressed against the zinc oxide ointment 26 around the wound, the polymer film is held securely in place. The zinc oxide ointment acts as a quasi gasket.

In another exemplary embodiment of the present invention, the composition for improved treatment of wounds on a patient further comprises a wax matrix. The wax matrix may be utilized in place of a dressing. Exemplary wax matrices include Bag Balm® available from Dairy Association Co. of Lyndonville, Vt., diaper rash ointment, Dermagran® available from Derma Sciences, vegetable shortening, petroleum jelly and zinc oxide ointment. One preferred wax matrix comprises a 40% (by weight) zinc oxide ointment.

In one embodiment, the composition further comprises a disinfectant compound to disinfect and dry a wound such as Dakin's solution (dilute hyperchloride or bleach). If odor control is desired, oil of wintergreen or other odor control agents can be added to the composition.

In another exemplary embodiment, the composition further comprises one or more enzymes for debridement such as collagenase (Santyl® available from Smith & Nephew), Accuzyme® and Panafil® both which are available from HealthPoint.

Another embodiment of the present invention comprises a wound dressing comprising a bandage, and a safe and effective amount of lidocaine in a carrier, wherein the wound dressing enhances healing of the wound. In an exemplary embodiment, the bandage comprises cotton, gauze, fiberglass or a synthetic material.

Another aspect of the present invention is a method for treating a patient having a skin wound. The method comprises locally administering a safe and effective amount of lidocaine in a carrier to the skin wound, such that the healing of the wound is enhanced. In one exemplary embodiment, the method further comprises covering the lidocaine composition in the skin wound with a dressing.

Yet another aspect of the present invention is an article of manufacture comprising packaging material and a composition comprising a safe and effective amount of lidocaine in a carrier, wherein the packaging material comprises a label that indicates the composition is useful for treating a patient having a skin wound, and wherein local administration of the composition enhances healing of the skin wound.

Another embodiment of the present invention is a pre-packaged wound dressing contained in a package, comprising a safe and effective amount of lidocaine in a carrier, and a bandage configured to cover a wound. In an exemplary embodiment, the lidocaine in the carrier is contained in a storage container. In another exemplary embodiment, the bandage is coated on at least one side with the lidocaine in the carrier. In another exemplary embodiment, the wound dressing is configured to deliver a controlled release of the composition to the wound bed at a predetermined rate for a predetermined time.

Another aspect of the present invention is a method for treating a patient having a skin wound comprising applying a mixture of lidocaine and a wax matrix directly on the wound. In one exemplary embodiment, the method further comprises applying a topical antibiotic powder on the lidocaine composition on the wound. In another exemplary embodiment, a polymer film is placed over composition on the wound bed and the composition is utilized to secure the polymer film to the patient.

EXAMPLE CASE STUDIES

Case One

Figure 7:
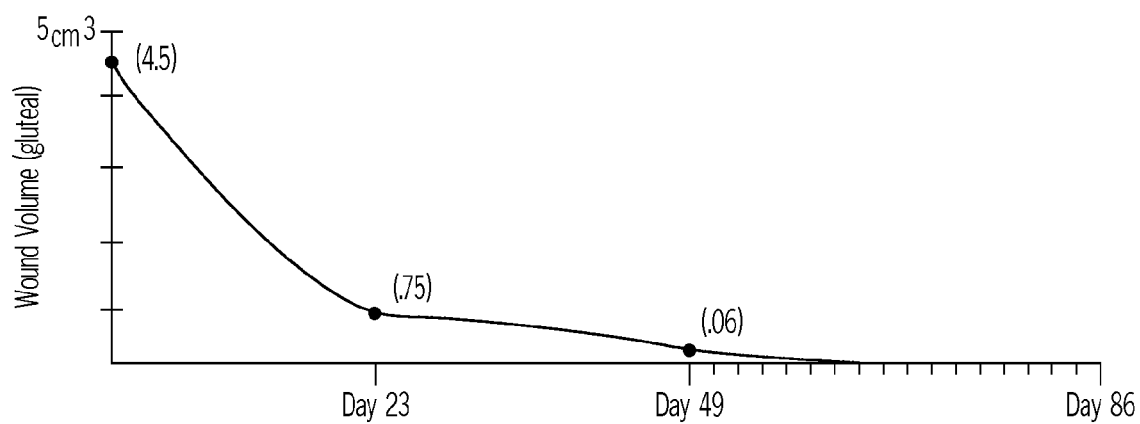
FIG. 7 sets forth wound treatment performance of the present invention relating to exemplary case study one.

A 91 year old white male hospice patient with end stage dementia. Wound on gluteal cleft had been worsening under prior treatment of Collagenase (Santyl®) and Polysporin® ointment (bacitracin zinc-polymyxin B). Prior to treatment with the method and composition of the present invention, the wound measured 4.5 cm$^3$ and was tender. Treatment consisted of initially packing gauze strips coated with 2% viscous lidocaine in the wound bed. After wound had reduced in size to prevent packing (23 days after initial treatment), dressing containing 2% viscous lidocaine was applied to wound. FIG. 7 depicts the results of treatment of the gluteal wound. As can be seen from astonishing results depicted in FIG. 7, the gluteal cleft wound was unexpectedly reduced in size by approximately 85% in 23 days and completely healed in less than 80 days utilizing the present invention.

Case Two

Figure 8:
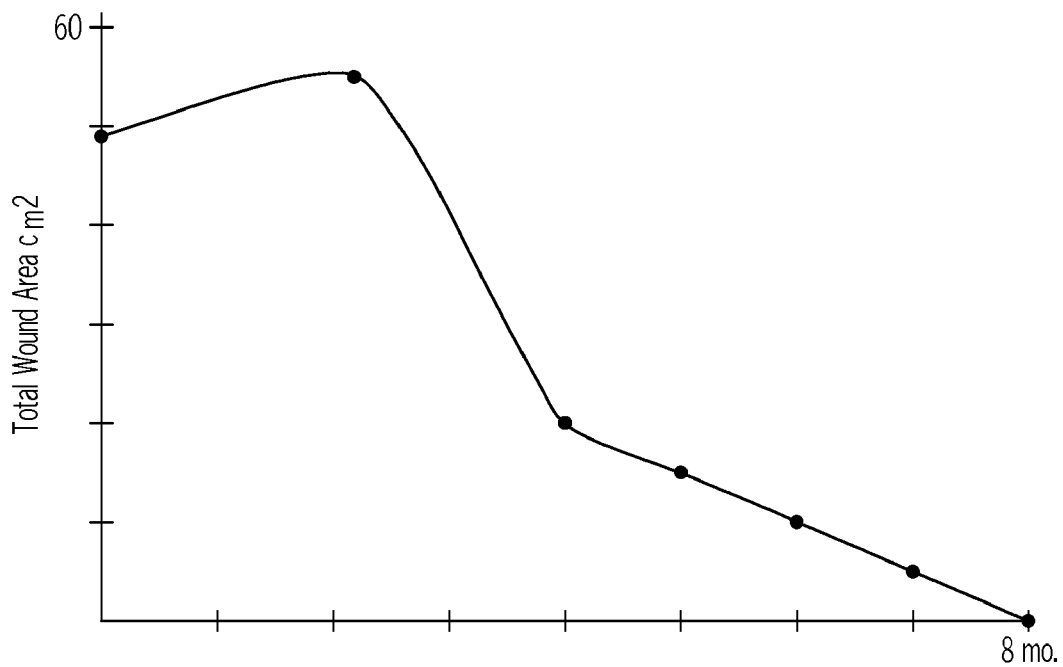
FIG. 8 sets forth wound treatment performance of the present invention relating to exemplary case study two.

A 86 year old white male with end stage renal disease and peripheral vascular disease had multiple non-healing wounds on the right leg. A heel wound had been surgically debrided and was non-healing. A traumatic injury to the right shin was non-healing. under prior treatment with Dakin's solution. Table 1 depicts the wounds and area size. Treatment utilized the present invention composition and method of a 2% viscous lidocaine solution with bacitracin zinc-polymyxin B powder. The composition comprised approximately 18-19.8 mg of lidocaine hydrochloride, 500-1000 units polymyxin B sulfate and 25-50 units of bacitracin zinc. The unexpected and astonishing results of the present invention are depicted in FIG. 8 which illustrates the amazing reduction in wound area on prior non-healing wounds.

TABLE 1

| | Wound Area ($cm^2$) during treatment by number of months | | | | | | | |
|---|---|---|---|---|---|---|---|---|
| Wound location | Before treatment utilizing present invention | 2 months* | 4 months | 5 months | 5.5 months | 6 months** | 7 months | 8 months |
| Shin | 15.75 | 24 | 16 | 12 | 10.0 | 12 | 4.4 | 0 (closed) |
| Lateral mall | 5.5 | 14 | 1 | <1 | 0 (closed) | 0 | 0 | 0 |
| heel | 22.75 | 9 | 0 (closed) | 0 | 0 | 0 | 0 | 0 |
| lateral foot | 3.94 | 7.5 | 2.4 | 0 (closed) | 0 | 0 | 0 | 0 |
| medial dorsum | 0.375 | .25 | 0 (closed) | 0 | 0 | 0 | 0 | 0 |

*Treatment between initial and 2 month time was not continuous. Wounds were debrided to remove eschars. Vascular surgeon recommended amputation.
**Shin wound became infected and treated with maggot therapy.

Case Three

Figure 9:
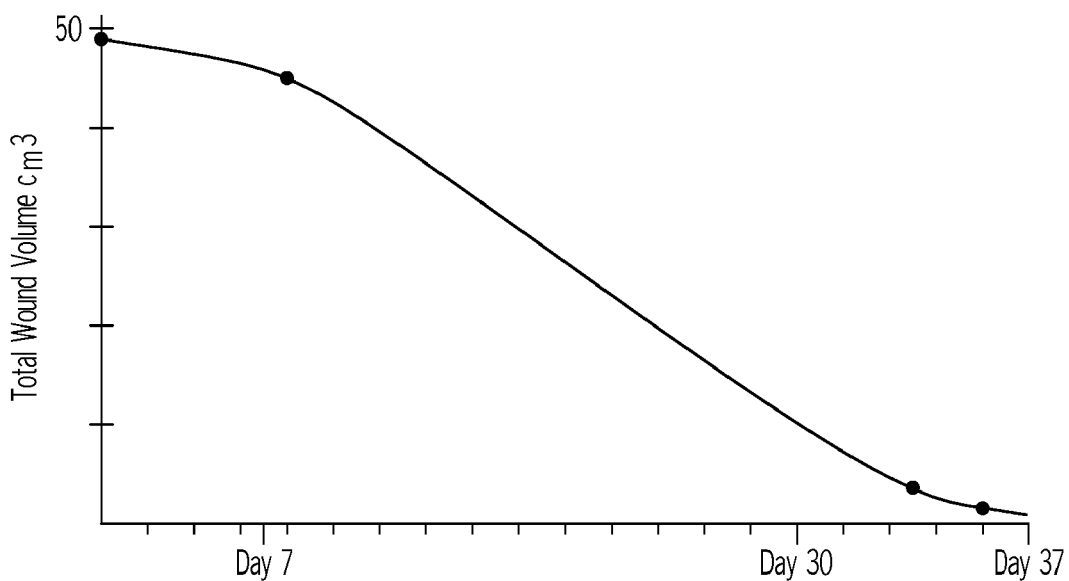
FIG. 9 sets forth wound treatment performance of the present invention relating to exemplary case study three.

A 40 year old white female hospice patient with end stage multiple sclerosis had a coccyx wound as well as multiple foot and leg wounds. Prior to treatment utilizing the present invention, the patient had 12 wounds with the coccyx wound having a surface area totaling 48 $cm^2$. Treatment utilized the composition and method of the present invention: a 2% viscous lidocaine solution with bacitracin zinc-polymyxin B powder. The composition comprised approximately 18-19.8 mg of lidocaine hydrochloride, 500-1000 units polymyxin B sulfate and 25-50 units of bacitracin zinc per gram of the composition. The unexpected and astonishing results of the present invention are depicted in FIG. 9 which illustrates the amazing reduction in wound volume with complete healing in under 60 days.

These case studies demonstrate that the compositions and methods according to the present invention exhibit surprising results in the mitigation or elimination of non-healing wounds on patients.

The foregoing description of the various embodiments of the invention has been presented for the purposes of illustration and description. It is not intended to be exhaustive or to limit the invention to the precise form disclosed. Many alternatives, modifications and variations will be apparent to those skilled in the art of the above teaching. Accordingly, this invention is intended to brace all alternatives, modifications and variations that have been discussed herein, and others that fall within the spirit and broad scope of the claims.

What is claimed:

1. A method for treating a patient having a pressure ulcer, comprising applying a healing composition to a primary dressing and locally administering the primary dressing with the applied healing composition to the pressure ulcer such that the healing of the pressure ulcer is enhanced;
   wherein the healing composition comprises:
   from about 5 mg to about 40 mg lidocaine hydrochloride per gram of the healing composition;
   from about 250 units to about 2000 units polymyxin B sulfate per gram of the healing composition; and
   from about 10 units to about 100 units bacitracin zinc per gram of the healing composition.

2. The method of claim 1, further comprising covering the primary dressing with the applied healing composition in the pressure ulcer with a secondary dressing.

3. The method of claim 2, wherein the primary dressing comprises cotton, gauze, fiberglass or synthetic material.

4. The method of claim 2 wherein the secondary dressing comprises a polymeric film.

5. The method of claim 1, wherein the healing composition comprises:
   from about 18 mg to about 25 mg lidocaine hydrochloride;
   from about 500 units to about 1000 units polymyxin B sulfate; and
   from about 25 units to about 50 units bacitracin zinc per gram of the composition.

6. The method of claim 1, wherein the healing composition comprises:
   from about 18 mg to about 20 mg lidocaine hydrochloride.

7. The method of claim 1, wherein the healing composition further comprises oil of wintergreen.

8. The method of claim 1, wherein the healing composition further comprises one or more enzymes for debridement.

9. A method for treating a patient having a pressure ulcer, comprising:
   applying a zinc oxide ointment around the exterior of the pressure ulcer;
   applying lidocaine and an antibiotic compound in a composition to a primary dressing;

applying the primary dressing to the pressure ulcer; and securing the primary dressing to the patient utilizing a secondary dressing and the applied zinc oxide ointment;

wherein the composition comprises:

from about 5 mg to about 40 mg lidocaine hydrochloride per gram of the composition;

from about 250 units to about 2000 units polymyxin B sulfate per gram of the composition; and from about 10 units to about 100 units bacitracin zinc per gram of the composition.

10. The method of claim 9, wherein the primary dressing comprises a packing material containing lidocaine and an antibiotic compound placed directly in the pressure ulcer.

11. The method of claim 9, wherein securing the primary dressing comprises placing a polymer film secondary dressing over the primary dressing and utilizing the zinc oxide ointment surrounding the exterior of the pressure ulcer to secure the polymer film secondary dressing to the patient.

12. The method of claim 9, further comprising applying a saline solution to the primary dressing if the pressure ulcer is dry.

13. The method of claim 9, wherein the composition comprises:

from about 18 mg to about 25 mg lidocaine hydrochloride;

from about 500 units to about 1000 units polymyxin B sulfate; and from about 25 units to about 50 units bacitracin zinc per gram of the composition.

14. The method of claim 9, wherein the composition further comprises oil of wintergreen.

15. The method of claim 9, wherein the composition further comprises one or more enzymes for debridement.

16. A method for treating a patient having a diabetic ulcer, comprising applying a healing composition to a primary dressing and locally administering the primary dressing with the applied healing composition to the diabetic ulcer such that the healing of the diabetic ulcer is enhanced;

wherein the healing composition comprises:

from about 5 mg to about 40 mg lidocaine hydrochloride per gram of the healing composition;

from about 250 units to about 2000 units polymyxin B sulfate per gram of the healing composition; and from about 10 units to about 100 units bacitracin zinc per gram of the healing composition.

17. A method for treating a patient having an ischemic ulcer, comprising applying a healing composition to a primary dressing and locally administering the primary dressing with the applied healing composition to the ischemic ulcer such that the healing of the ischemic ulcer is enhanced;

wherein the healing composition comprises:

from about 5 mg to about 40 mg lidocaine hydrochloride per gram of the healing composition;

from about 250 units to about 2000 units polymyxin B sulfate per gram of the healing composition; and from about 10 units to about 100 units bacitracin zinc per gram of the healing composition.

18. A method for treating a patient having a diabetic ulcer, comprising:

applying a zinc oxide ointment around the exterior of the diabetic ulcer;

applying lidocaine and an antibiotic compound in a composition to a primary dressing;

applying the primary dressing to the diabetic ulcer; and securing the primary dressing to the patient utilizing a secondary dressing and the applied zinc oxide ointment;

wherein the composition comprises:

from about 5 mg to about 40 mg lidocaine hydrochloride per gram of the composition;

from about 250 units to about 2000 units polymyxin B sulfate per gram of the composition; and from about 10 units to about 100 units bacitracin zinc per gram of the composition.

19. A method for treating a patient having an ischemic ulcer, comprising:

applying a zinc oxide ointment around the exterior of the ischemic ulcer;

applying lidocaine and an antibiotic compound in a composition to a primary dressing;

applying the primary dressing to the ischemic ulcer; and securing the primary dressing to the patient utilizing a secondary dressing and the applied zinc oxide ointment;

wherein the composition comprises:

from about 5 mg to about 40 mg lidocaine hydrochloride per gram of the composition;

from about 250 units to about 2000 units polymyxin B sulfate per gram of the composition; and from about 10 units to about 100 units bacitracin zinc per gram of the composition.

* * * * *